(12) United States Patent
Sharpe

(10) Patent No.: US 7,007,237 B1
(45) Date of Patent: Feb. 28, 2006

(54) METHOD AND SYSTEM FOR ACCESSING WEB PAGES IN THE BACKGROUND

(75) Inventor: Timothy David Sharpe, Redmond, WA (US)

(73) Assignee: Microsoft Corporation, Redmond, WA (US)

( * ) Notice: Subject to any disclaimer, the term of this patent is extended or adjusted under 35 U.S.C. 154(b) by 542 days.

(21) Appl. No.: 09/563,371

(22) Filed: May 3, 2000

(51) Int. Cl.
G06F 9/00 (2006.01)

(52) U.S. Cl. ............... 715/764; 715/748; 715/745; 715/760; 715/835; 715/853; 715/854

(58) Field of Classification Search ............ 345/764, 345/748, 866, 700, 745, 760, 835, 853, 854, 345/749; 709/203, 217, 219
See application file for complete search history.

(56) References Cited

U.S. PATENT DOCUMENTS

| | | | | |
|---|---|---|---|---|
| 5,572,643 A | * | 11/1996 | Judson | 709/218 |
| 5,802,292 A | * | 9/1998 | Mogul | 709/203 |
| 6,085,226 A | * | 7/2000 | Horvitz | 709/203 |
| 6,097,390 A | * | 8/2000 | Marks | 345/772 |
| 6,157,933 A | * | 12/2000 | Celi et al. | 715/501.1 |
| 6,385,641 B1 | * | 5/2002 | Jiang et al. | 709/203 |
| 6,393,526 B1 | * | 5/2002 | Crow et al. | 711/137 |
| 6,457,025 B1 | * | 9/2002 | Judson | 715/501.1 |

* cited by examiner

Primary Examiner—Kristine Kincaid
Assistant Examiner—Peng Ke
(74) Attorney, Agent, or Firm—Merchant & Gould P.C.

(57) ABSTRACT

A method and system that allows the user to fetch a subsequent web page while maintaining the current web page as the active web page. The next web page is fetched "in the background" and stored in cache memory without interrupting the user. Once the requested web page has been stored in cache, an indicator is added to the history list allowing the user access to the processed web page. In order to view the next web page, the user simply selects the appropriate icon on the user interface, such as the forward button which is akin to selecting the back or forward button to scroll through the history of web pages. Since the web page is in the cache, it is displayed relatively quickly and since the user selects when to display the page, there is no interruption.

18 Claims, 7 Drawing Sheets

METHOD AND SYSTEM FOR ACCESSING WEB PAGES IN THE BACKGROUND

TECHNICAL FIELD

The present invention relates to graphical user interfaces, and particularly to Internet browser user interfaces. More particularly still, the present invention relates to the display of "web" pages while receiving new or updated web pages on relatively small computing devices.

BACKGROUND OF THE INVENTION

Small, handheld computing devices have been steadily growing in popularity in recent years. The devices are known by different names, such as palmtops, pocket computers, personal digital assistants, personal organizers, H/PCs, or the like. These devices, hereinafter "small computer devices," provide much of the same functionality as their larger counterparts. In particular, the small computer devices provide users the ability to perform word processing, task management, spreadsheet processing, address book functions and email functions, as well as many other functions. Additionally, small computer device users frequently connect to, and communicate over, the Internet from various remote locations.

The Internet is a distributed, worldwide computer network comprising computers belonging to various entities such as corporations, institutes of learning, and research organizations. The "worldwide web" or "web" is a specific Internet network using a specific Internet protocol, i.e., Hyper Text Transfer Protocol (HTTP). Servers that use the web are known as web servers and typically provide many separate electronic files, displays or documents, known as web pages, that are accessible to other web servers or web clients. These web pages are identified by a uniform locator (URL), which is a type of address that allows a user to request the item.

For communication over the Internet, operating systems in the small computer devices typically include browsers or browser functionality. Browsers provide many functions including a graphical user interface that allows the user to both enter a request for a web page and view the response once the web page is received from the web server. Additionally, the browser provides the ability to process an incoming web page, typically in HTML format into a displayable form so that the page can be displayed on the computer. The process of requesting web pages using a browser is generally referred to as either navigating or browsing the web since it is relatively simple to jump from one web server to the another using the Internet's HTTP protocol.

Although extremely functional, small computer devices unfortunately suffer certain drawbacks as compared with larger, desktop computers. One such drawback relates to the slower modem speeds for Internet access and slower processors for processing web pages. Therefore, browsing the web typically involves long periods of time between requesting a web page and being able to view the web page. Moreover, while the browser is requesting, receiving and processing the next page, a blank screen or white space is displayed to the user. Given the long time between web pages users are continually frustrated.

To lessen the time between requesting a page and viewing the requested page, some browsers utilize progressive rendering, which allows for the display of portions of the web page as they are processed. For example, if the text for a page has been processed but the figures or graphics have not, a progressive rendering browser may display the text while the remaining portions are still being processed. Although progressive rendering reduces the wait period for some information it does not eliminate the entire waiting period since the graphics must still be processed.

Larger computer browsers partially solve this "white space" problem by allowing users the option of opening a newly requested or subsequent web page in a different window. This feature allows the user to continue to view the current web page while the next web page is being downloaded, processed and displayed, in another window. Once the display is processed in the other window, the user switches active windows to the next web page. The solution only partially solves the problem since the user does not know when the second window is done processing the second page and the user must switch to the second window which requires window manipulation. Moreover, the small computer devices only provide a single window interface. Therefore, when using the smaller computers, the browser must display the new web page in the window used to display the last web page and thus the option of opening the next web page in a new window is simply not available.

A previous solution to this problem relates to pre-fetching web pages. In general, pre-fetching is a process whereby the browser guesses which web page will be requested next by the user. For example, if the user opens a web page having five links on the page, the browser guesses that the user will request one of the five links, such as the first link. In this scenario, the browser begins requesting the web page associated with the first link. The browser may fetch and store the entire web page in cache, purely on the notion that the user might select that link. If the user selects the link, then the page can be displayed relatively quickly. However, due to the guesswork involved, the process is not a satisfactory solution, as much of the pre-fetched information is not displayed. Moreover, since many cell phone companies charge by the byte, i.e., charge the user by the amount of information requested and downloaded to the computer, pre-fetching is inappropriate since much of the information paid for is never viewed.

Another drawback associated with some known browsers is that once a request for a web page is made, the user has no control over the current display. Often, a user makes a request but the display doesn't go blank for a short period of time. During this time, the user may become interested in the current display such that when the next page is finally displayed, it amounts to a significant interruption to the user.

It is with respect to these considerations and others that the present invention has been made.

SUMMARY OF THE INVENTION

The present invention solves the above identified problems and other problems by providing a browser feature that allows the user to fetch the next web page while maintaining the current web page as the active web page. The next web page is fetched "in the background" and stored in cache memory without interrupting the user. Once the requested web page has been stored in cache, an indicator is added to the history list allowing the user access to the processed web page. In order to view the next web page, the user simply selects the appropriate icon on the user interface, such as the forward button which is akin to selecting the back or forward button to scroll through the history of web pages. Since the web page is in the cache, it is displayed relatively quickly and since the user selects when to display the page, there is no interruption.

The invention may be implemented as a computer process, a computing system or as an article of manufacture such as a computer program product. The computer program product may be a computer storage medium readable by a computer system and encoding a computer program of instructions for executing a computer process. The computer program product may also be a propagated signal on a carrier readable by a computing system and encoding a computer program of instructions for executing a computer process.

An embodiment of the present invention is a method of displaying a subsequent page in place of a current page in a window of a graphical user interface on the computer display. The method comprises the steps of receiving a process request for the subsequent page and processing the subsequent page into displayable form in memory. Once the page has been processed, a visual cue is displayed indicating that the subsequent page has been processed. Upon receipt of an indication from the user that the subsequent page should be displayed, the subsequent page is displayed in the current window from memory. In accordance with other aspects, the method provides a visual cue to the user once a page has been substantially processed. Additionally, the displayed page may be a web page and the computer is a client computer system that is connected to a server computer that receives a request for the web page from the client computer and returns the web page to the client computer.

In accordance with other preferred aspects, the method further comprises the steps of receiving multiple requests for web pages to be fetched in the background and upon receipt of each request for a web page, adding the requested web page to a history list. The history list is made accessible to the user, allowing the user to select a web page for display from the web page. If an error is returned to the computer in place of a requested web page, the web page is removed from the history list and a visual indication is provided to the user that the requested web page is inaccessible.

A more complete appreciation of the present invention and its improvements can be obtained by reference to the accompanying drawings, which are briefly summarized below, to the following detail description of presently preferred embodiments of the invention, and to the appended claims.

DETAILED DESCRIPTION OF THE INVENTION

An embodiment of the invention provides for the requesting, downloading and processing of a requested web page in the background such that the user may continue to view the present web page without interruption while the new page is being processed. Once the new web page is ready to be displayed, a visual cue is provided to the user. The user may then simply indicate the desire to display the new page. Once indicated, the browser of the present invention replaces the existing web page with the newly requested web page. The user has control over which web page is being displayed and less time is wasted viewing a substantially blank display or "white space."

The logical operations of the various embodiments of the present invention are implemented (1) as a sequence of computer program steps or program modules running on a computing system and/or (2) as interconnected machine logic or hardware modules within the computing system. The implementation is a matter of choice dependent on the performance requirements of the computing system implementing the invention. Accordingly, the logical operations making up the embodiments of the present invention described herein are referred to alternatively as operations, steps or modules.

Figure 1:
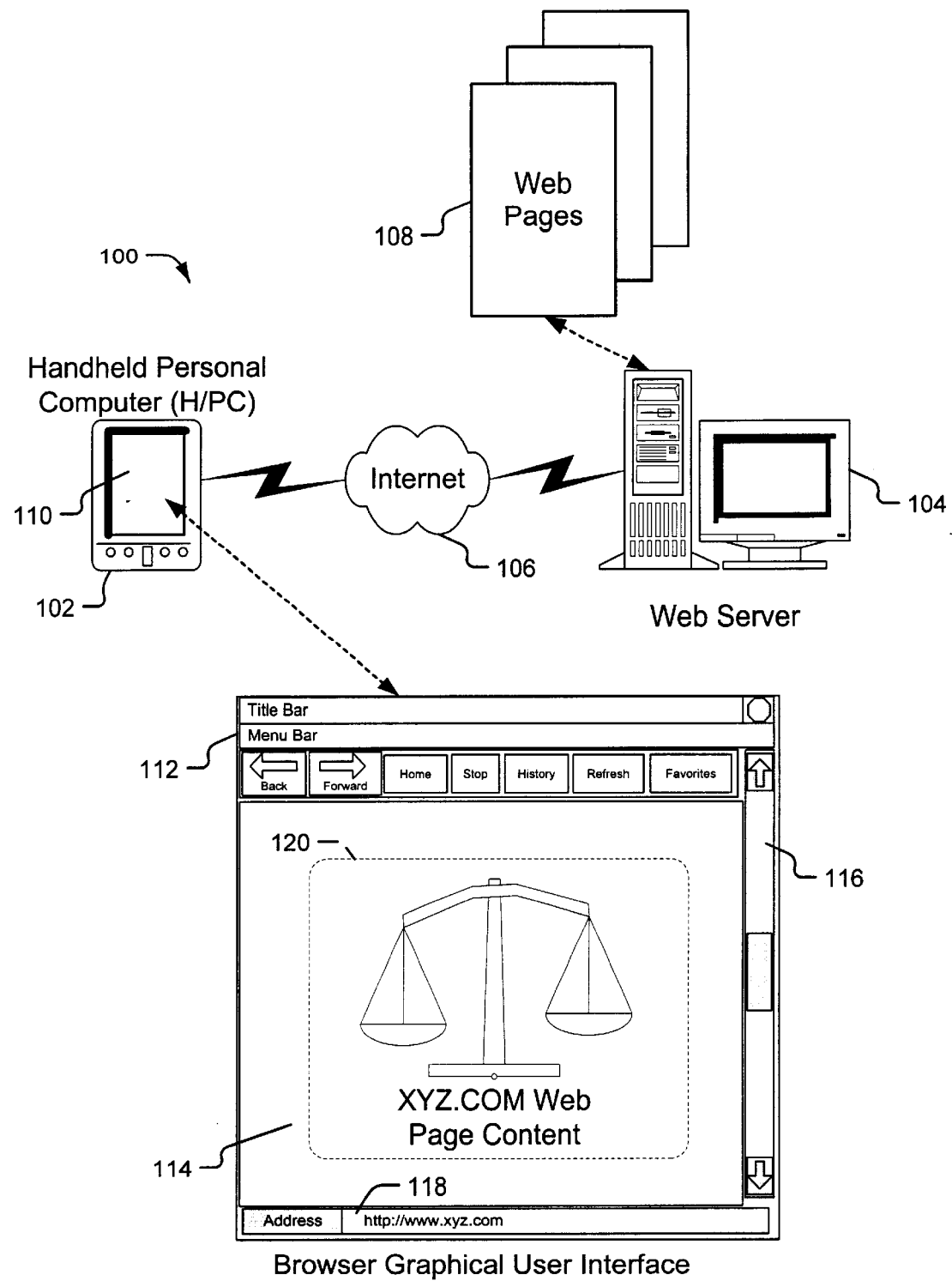
FIG. 1 illustrates a system showing the internet and a small device capable of the present invention.

A client/server network system 100 comprising a client computer system 102, which is connected to a server computer system 104 through the Internet 106, is shown in FIG. 1. In the illustrated client-server environment 102 the client computer system 102 connects to the computer network 106 over a telephone line with a modem (not shown). Alternatively, the computer 102 may connect using other network connection technologies. Moreover, the invention can alternatively be embodied in a client-server environment for other public or private computer networks, such as computer network of a commercial on-line service or an internal corporate local area network (LAN) or like computer networks.

The server 104 is an Internet server that is also connected to the Internet. The server 104 generally sends requested electronic items, such as web pages 108, through various connections or gateways to other computer systems, such as the client computer system 102. Web pages 108 are electronic documents that reside on the server computer 104. In conformance with HTML, the web page can incorporate text and other additional information content, such as images, audio video executable programs, among others. The web pages 108 may also incorporate the "hyper-links" that specify the location of other web pages or files located on the same or other server computers. In alternative network protocol embodiments of the invention the web page 108 can have other structured document formats.

To facilitate the Internet communications, the computer 102 runs a browser module (hereinafter browser) as part of the operating system on the computer 102 for retrieving or browsing web pages 108, or other electronic documents from the remote server computer 104. The browser on the computer 102 retrieves an electronic document 108 from a web site, i.e., the web server 104 on the Internet 106, and displays the document on the computer screen or output device 110 (FIG. 1). To view the web page 108, the user specifies a URL related to the particular document 108, such as by entering a URL character string using an user input interface, by selecting a hyperlink specifying the URL in an HTML document currently being displayed in the browser display 110, or by selecting a URL from a list provided by the browser. In response to the entered URL, the browser generates a request command for the URL and transmits the request on the Internet 106 for the document 108 using conventional Internet protocols, such as the Hypertext Transport Protocol (HTTP).

In one preferred embodiment, the browser utilizes a graphical interface, generating the rectangular viewing or display 112 on the screen 110 of the computer's output device as is conventional in an operating system with a graphical user interface. The browser display 112 includes a frame with graphical interface user controls (e.g. menu bar, scroll bars, buttons, etc.) which generally surround a content area 114 in the display 112. The user can activate the user interface controls for the frame with the input device to control the browser, e.g., touching an icon represented on a touch screen selects the icon.

The browser displays the content of the current web page, such as content 120, in the document display area 114. If the electronic document is too large to completely fit within the document area 114 the browser displays a portion of the document referred to hereafter as the "visible portion" in the document area 114 and presents the scroll bar 116. The user can manipulate the scroll bar 116 with a mouse or other pointing device or other input device to change the visible portion of the document that is shown by the browser within the document display area 114. The display 112 also comprises an address bar 118, which displays the URL for the web page 108 currently being displayed in document area 114.

In one embodiment of the present invention, the client computer system 102 is a portable small computing device comprising a browser in an operating system capable of executing the operations of the present invention. The client computer system 102 may also be a notebook sized computer or some other small computing platform and may even be a larger computer system such as those typically identified as a desktop computers.

Figure 2:
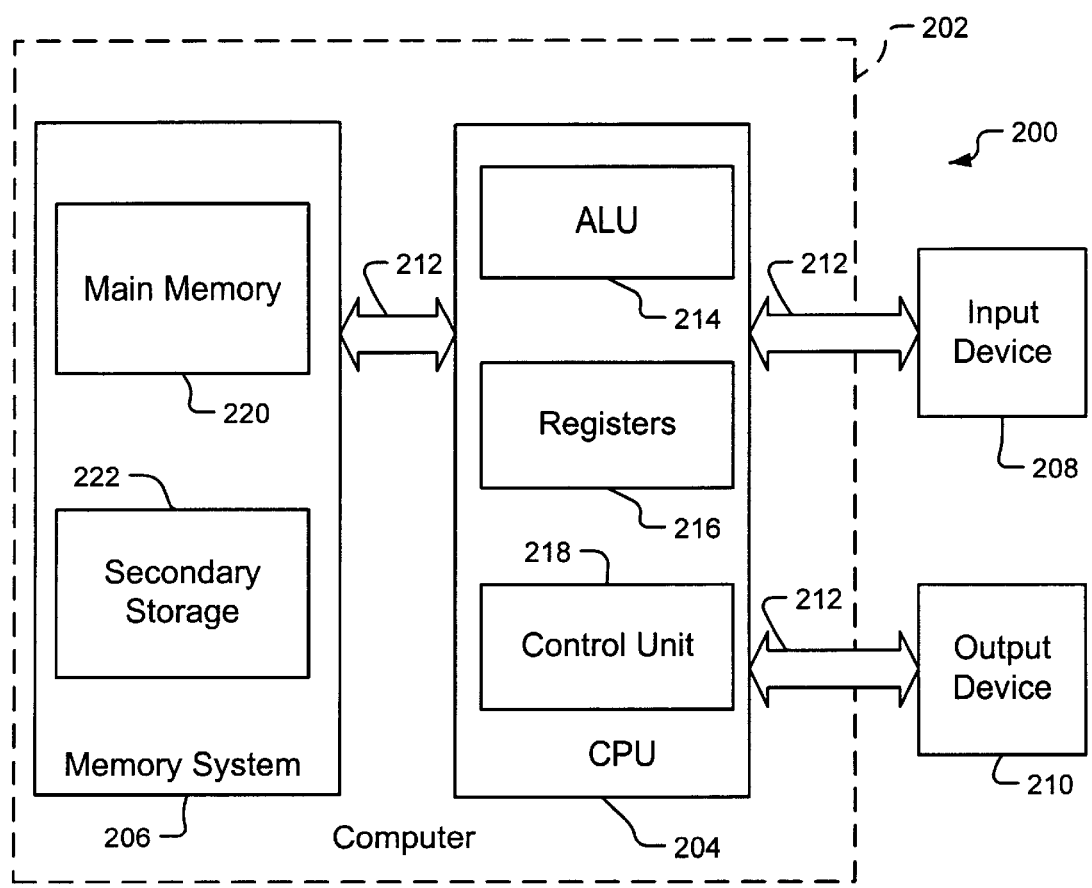
FIG. 2 is block diagram of a computer such as the small device shown in FIG. 1.

More specifically, the computer 102 incorporates a system 200 of resources for implementing an embodiment of the invention, as shown in FIG. 2. The system 200 incorporates a computer 202 having at least one central processing unit (CPU) 204, a memory system 206, an input device 208, and an output device 210. These elements are coupled by at least one system bus 212.

The CPU 204 is of familiar design and includes an Arithmetic Logic Unit (ALU) 214 for performing computations, a collection of registers 216 for temporary storage of data and instructions, and a control unit 218 for controlling operation of the system 200. The CPU 204 may be a microprocessor having any of a variety of architectures including, but not limited to those architectures currently produced by Intel, Cyrix, AMD, IBM and Motorola.

The system memory 206 has a main memory 220, in the form of media such as random access memory (RAM) and read only memory (ROM), and may incorporate or be adapted to connect to secondary storage 222 in the form of long term storage mediums such as hard disks, floppy disks, tape, compact disks (CDs), flash memory, etc. and other devices that store data using electrical, magnetic, optical or other recording media. The main memory 220 may also comprise video display memory for displaying images through the output device 208, such as a display screen. The memory can use a variety of alternative components having a variety of storage capacities such as magnetic cassettes, memory cards, video digital disks, Bernoulli cartridges, random access memories, read only memories and the like may also be used in the exemplary operating environment. Memory devices within the memory system and their associated computer readable media provide non-volatile storage of computer readable instructions, data structures, programs and other data for the computer system.

The system bus 212 may be any of several types of bus structures such as a memory bus, a peripheral bus or a local bus using any of a variety of bus architectures.

The input and output devices are also familiar. The input device can comprise a small keyboard, a mouse, a microphone, a touch pad, a touch screen, etc. The output devices can comprise a display such as display 110 (FIG. 1), a printer, a speaker, a touch screen, etc. Some devices, such as a network interface or a modem can be used as input and/or output devices. The input and output devices are connected to the computer through system buses 212.

The computer system 200 also has an operating system and usually one or more application programs. The operating system includes a set of programs that control the operation of the system 200, control the allocation of resources, provide a graphical user interface to the user, facilitate access to local or remote information, and may also include certain utility programs such as the email system. An application program is software that runs on top of the operating system software and uses computer resources made available through the operating system to perform application specific tasks desired by the user. In general, the browser is a part of the operating system that is responsible for retrieving web pages in accordance with the present invention, but the invention may be separately incorporated into an application that uses the operating system to connect to the Internet. Exemplary operating systems in which the browser of the present invention may be integrated with include Microsoft Corporation's Windows CE operating system for handheld personal computers.

Figure 3:
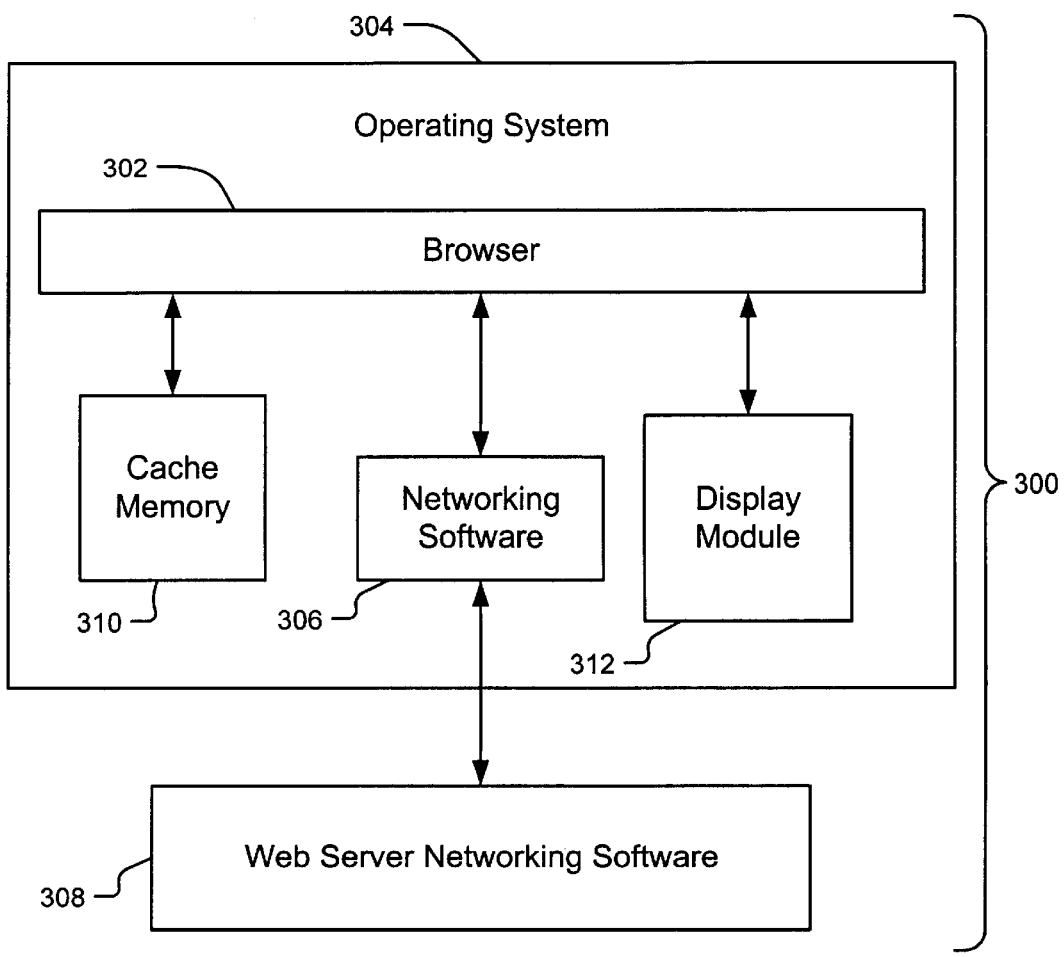
FIG. 3 is a block diagram of software environment capable of executing the present invention.

A software operating environment 300 capable of achieving the functions of the present invention is shown in FIG. 3. The environment 300 includes a browser module 302 and an operating system 304. In another preferred embodiment, the browser 302 is integrated into the operating system 304 as shown in FIG. 3. Alternatively, the browser 302 could be a separate application that communicates with the operating system 304.

The operating system 304 also has networking software 306 which implements networking protocols for communicating on the Internet 106, and thus indirectly with the network server software 308. For example, the operating system 304 in the illustrated embodiment may be Microsoft Corporation's Windows CE operating system, which uses a remote network access subsystem, a TCP/IP network protocol drivers, and a network adapter driver as the networking software 306 for communicating on the Internet. The browser 302 communicates with the networking software 306 using a set of application programming interfaces (APIs—not shown) of operating system functions and services to retrieve web pages 108 from the web server 104 (FIG. 1).

In operation, following a request for a web page 108, the browser module 302 receives a response from the networking software module 306 related to the actual response communicated by the web server 104 (FIG. 1). The response typically comprises at least a header and a body, wherein the body is an HTML document incorporating many of the web page display features including text, graphics, hyperlinks, etc.

Once the response is received, the browser processes or compiles the response, and in particular, the HTML document into object-type code or other displayable form that is stored in cache memory 310. Alternatively the browser 302 simply stores the body of the response in memory. Following the compiling phase, the web page is ready to be "rendered" to the display screen on the computing device housing the browser 302. Displaying the page from memory is relatively quick once the page has been processed. Additionally, the memory 310 along with other buffers and memory is large enough to store both the current web page and the subsequent web page. Moreover, if more than one web page is requested at a time, then the memory should be large enough to handle additional web pages.

In order to display or render the web page to the display 110 (FIG. 1), the browser communicates the code to a display module 312, which performs the display function. The browser 302 may communicate the code by way of passing a pointer or other reference to the display module 312 with a request to begin displaying the code associated with the received web page. Importantly, the browser module 302 of the present invention does not request the display module to render the web page until the browser module 302 has received an indication that the subsequent page should be displayed, wherein the indicating control signal may be conducted to the browser by the user, or by some other mechanism. In an embodiment the user supplies the indication by selecting or clicking the "forward" button or some other use interface control. Alternatively the indication may be in the form of no user interaction. That is, following the visual cue, an internal timer may begin counting down to zero. Once the time reaches zero the display automatically switches to the subsequent page, as long as no user interaction occurs. Thus, the next page acts like a screen saver, any input, like scrolling, stops the timer and the user must then select the forward button or otherwise indicate that the next page should be displayed. The timer may be configured by the user for a time period, e.g., five seconds. The time period should be long enough to allow user intervention, to stop the display of the next page, if desired.

During the browsing process, the browser 302 stores, in a buffer or in cache 310 a history list of recently viewed or visited web pages. The list is typically a list of URL references but may also contain pointers to the object type code for the web page located in cache. The cache may operate on a First In, First Out basis so the most recently viewed pages remain in the cache memory. Thus, if a user desires to view a previously viewed page that is still in cache, the browser recognizes that it is in the cache 310 and displays the web page without requesting it from the web server. Alternatively the request is still made, but the user can see what is in cache while the request is made and is being processed. Moreover, the display process is relatively quick if the page is in cache since it has been compiled, and no further processing (other than actual rendering) of the web page is required. Although most new web pages are added to the end of the history list, some may be inserted in the middle. That is, the web pages are added to the history list based on the current web page such that if the user scrolls back through the history list, and then requests a new page, the new page may be inserted into the history list following the current web page but before some of the existing list entries.

Figure 4:
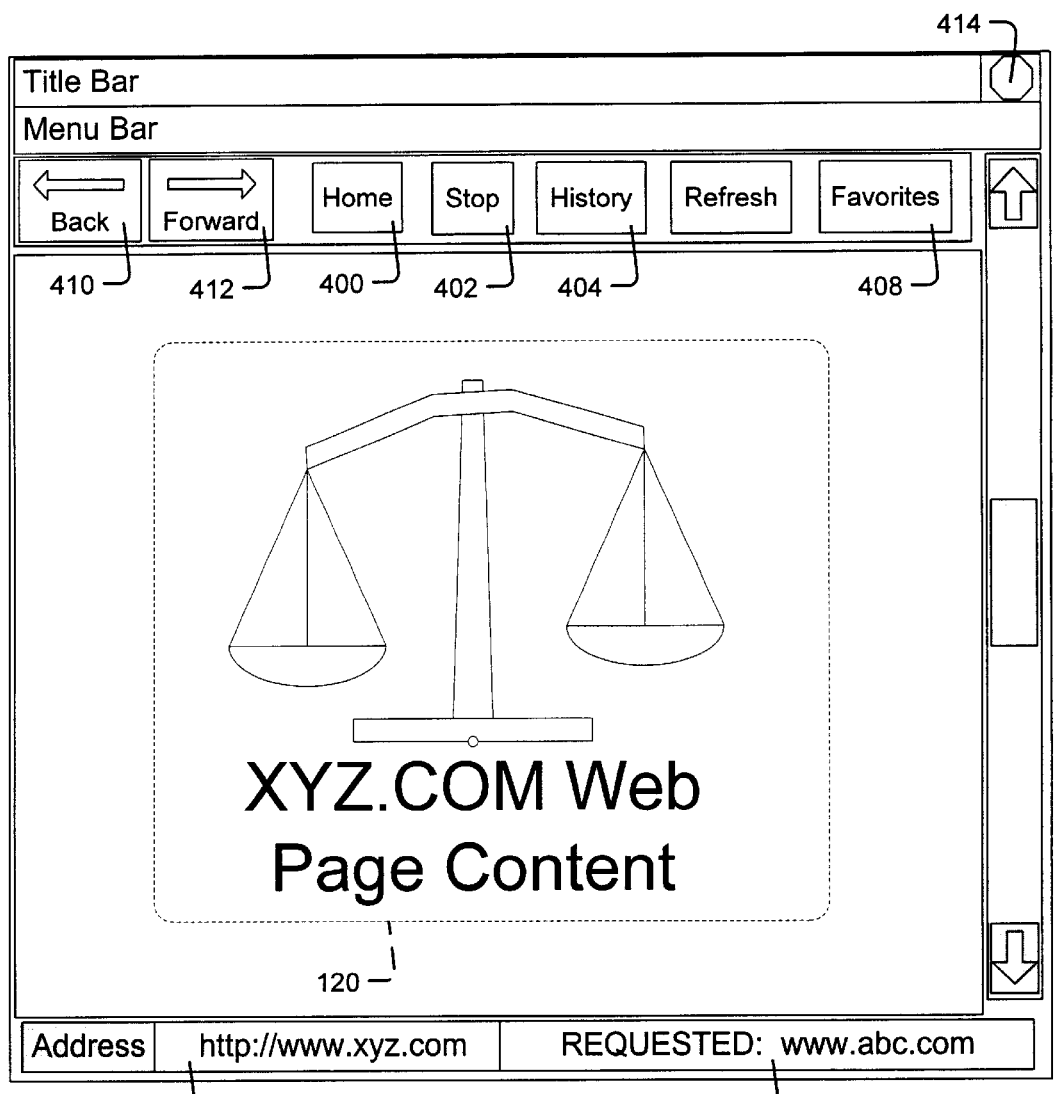
FIG. 4 is a screen shot illustrating a sample browser display.

FIG. 4 is an enlarged illustration of the browser display 112 shown in FIG. 1 having display area 114, scroll bar 116 and address bar 118. Display 112 further comprises conventional user-interface controls 400, 402, 404, 406, 408, 410 and 412. Although these controls are not necessary to browse the Internet, they provide useful functions that improve the user's browsing experience. For example, Home control 400 typically provides the user quick access to a home page, wherein selecting the control 400 initiates a command to the browser to fetch and display a predetermined web page, i.e., the user's home web page. Stop control 402 provides the user the ability to stop current processing of a web page, if desired. History control 404 provides the user access to a list of recently visited web sites. Refresh control 406 requests that the current web page be requested again from the web server to allow for updated information. Favorites control 408 provides the user quick access to certain "favorite" web pages, wherein selecting control 408 causes a list or menu of web pages to be displayed for selection by the user and wherein selecting a page from the menu initiates a command to the browser to fetch that web page. Of course, the user may enter these web pages using other conventional means to initiate the fetch process, the controls only provide shortcuts for the user. These controls therefore provide the user predetermined user-interface functions to help improve the browsing experience. In alternative embodiments, other controls that may be placed on the display 112.

In addition to the controls 400, 402, 404, 406 and 408, the browser display 112 also includes Back control 410 and forward control 412, which provide certain beneficial functionality to the user related to a browser's history. The Back control 410 takes advantage of the fact that the browser 302 (FIG. 3) keeps track of previously viewed web pages in a "history list" and allows the user to "go back" to the web page displayed prior to the current web page. That is, when the Back control 410 is selected, the browser automatically initiates a command to fetch and display the web page at the "top" of the history list, or the next item in the list if scrolling through the list. Therefore, the user can scroll through past web pages, in the order they were viewed. For example, assume that a user views their home page and then views a different commercial web page. If the user were then to select the Back control 410, the browser examines the history list, determines that the user's home page was the most recently viewed page on the history list, and automatically causes the home page to be displayed on the display. Typically, once the user has reached the end of the history list, the Back control 410 becomes inactive, which is indicated to the user through the use of a change color in the Back control 410. Often, the control 410 is "grayed out" to indicate to that it is inactive.

Scrolling through the history list using the Back control 410 causes the Forward control 412 to be activated. That is the user may scroll forward through the history list as well as backward.

As shown in FIG. 4, the display 112 displays the current web page, such as "www.xyz.com" 120 in display area 114. Once a new web page is requested, by the user, the browser 302 begins the requesting process and provides a visual cue to the user on display 112, that the request has been accepted, but does not erase the current display 120. The visual cue provided to the user may be an icon or an animation, or a "new page" address bar 416. In essence any number of visual cues can be presented on 112 to indicate that the next page is processing. In addition, the next page may be added to the history list. Alternatively the history list may be updated following the processing of the web page.

Figure 5:
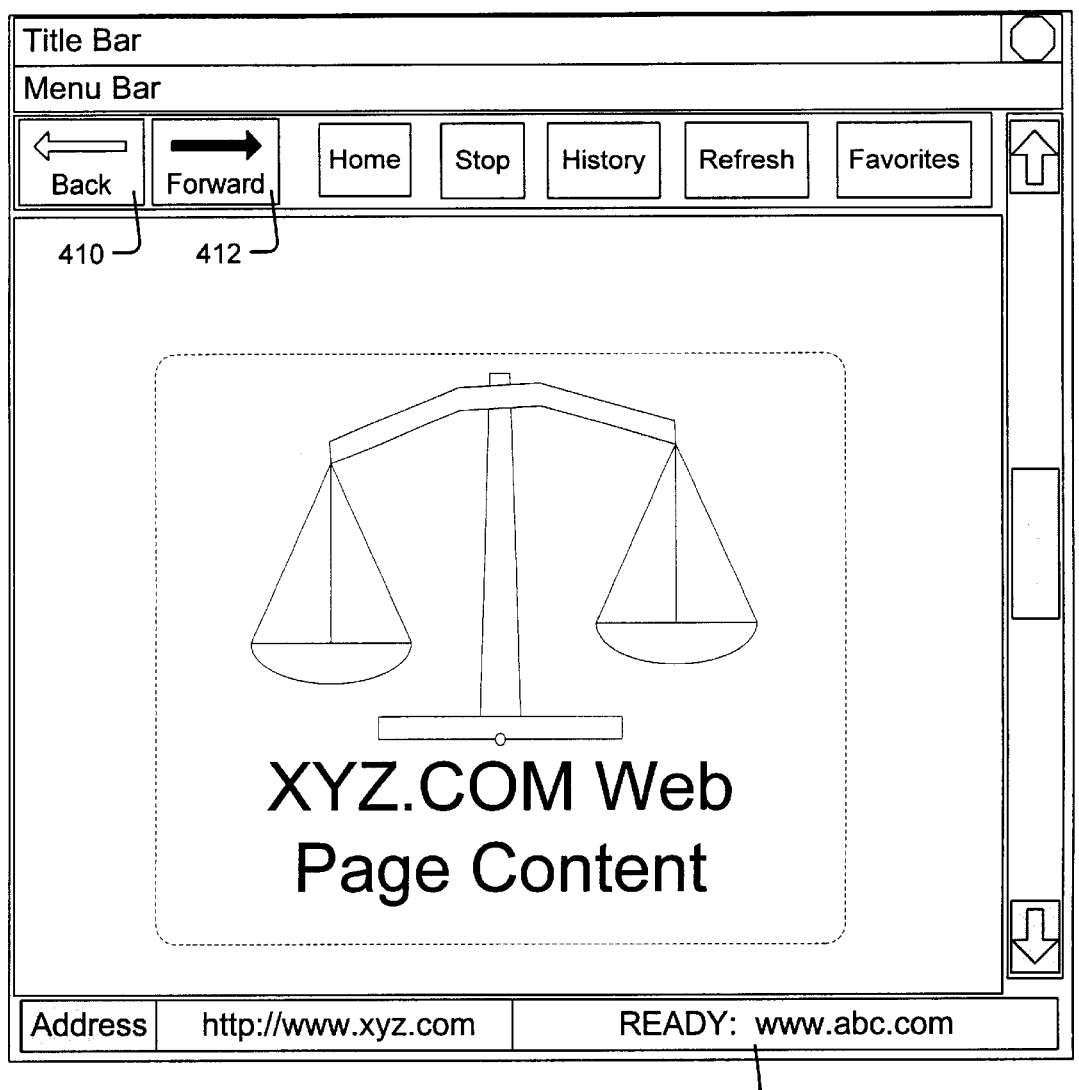
FIG. 5 is a browser display following the processing of a subsequent web page.

Once the web page is processed the page is added to the history list (if not added previously) and Forward control 412 is activated as shown in FIG. 5. Changing the color for the control 412 indicates activating the Forward control 412. Therefore, the color change for the control 412 also indicates that the web page is ready to be displayed.

Figure 6:
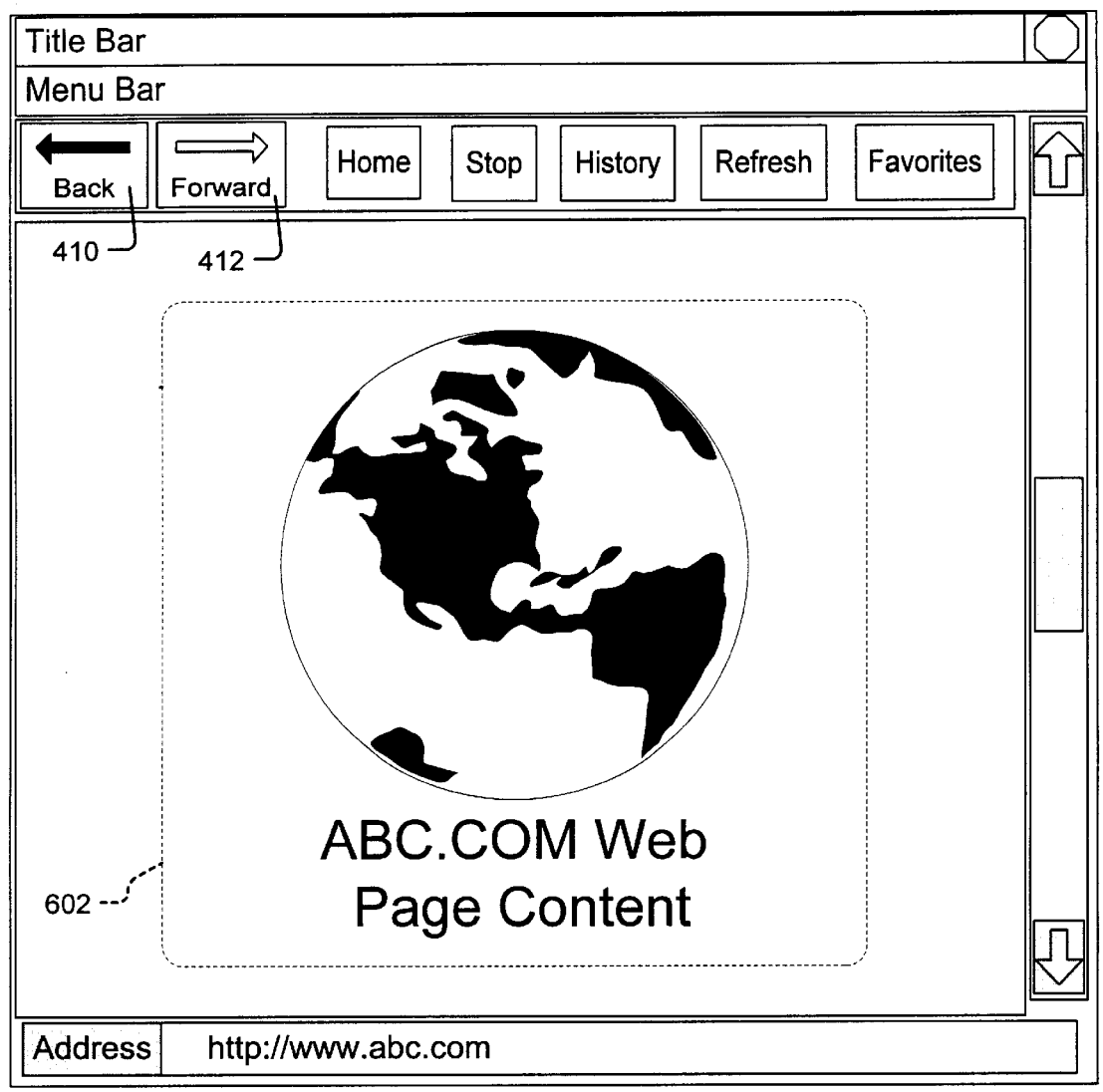
FIG. 6 is a browser display following selection of a display icon to cause the subsequent web page to be displayed.

The user selects the Forward control 412, the next requested web page is displayed, such as the sample web page 602 for "ABC.COM," as shown in FIG. 6. Forward control 412 becomes inactive after the subsequent web page is displayed and preferably grayed out to indicate its inactive status.

In alternative embodiments, if a user selects or requests multiple web pages at one time. As each web page is processed, it is added to the forward portion of the history list. Viewing an item from the forward list causes that item to be moved to the back list. In such a case, viewing one of the web pages does not inactivate the forward button 412 unless that item is the last item on the forward list. That is, as long as there are web pages in the forward list that have not been viewed, the forward button is active.

Although the color or shading change for the Forward control 412 is one method of announcing to the user that the next web page is ready for display, other announcement mechanisms may be used. For example, an icon may be displayed, the entire display may flash, a "next page" address bar may be displayed. Additionally, if the next web page was requested using a hyperlink in the existing web page, the link color can be modified to indicate the requested web page status as ready for viewing. In accordance with hyperlinks, a context menu may be displayed for the link, wherein the context menu allows the user to stop processing if the processing is not complete, or view the next web page if the processing is complete.

Figure 7:
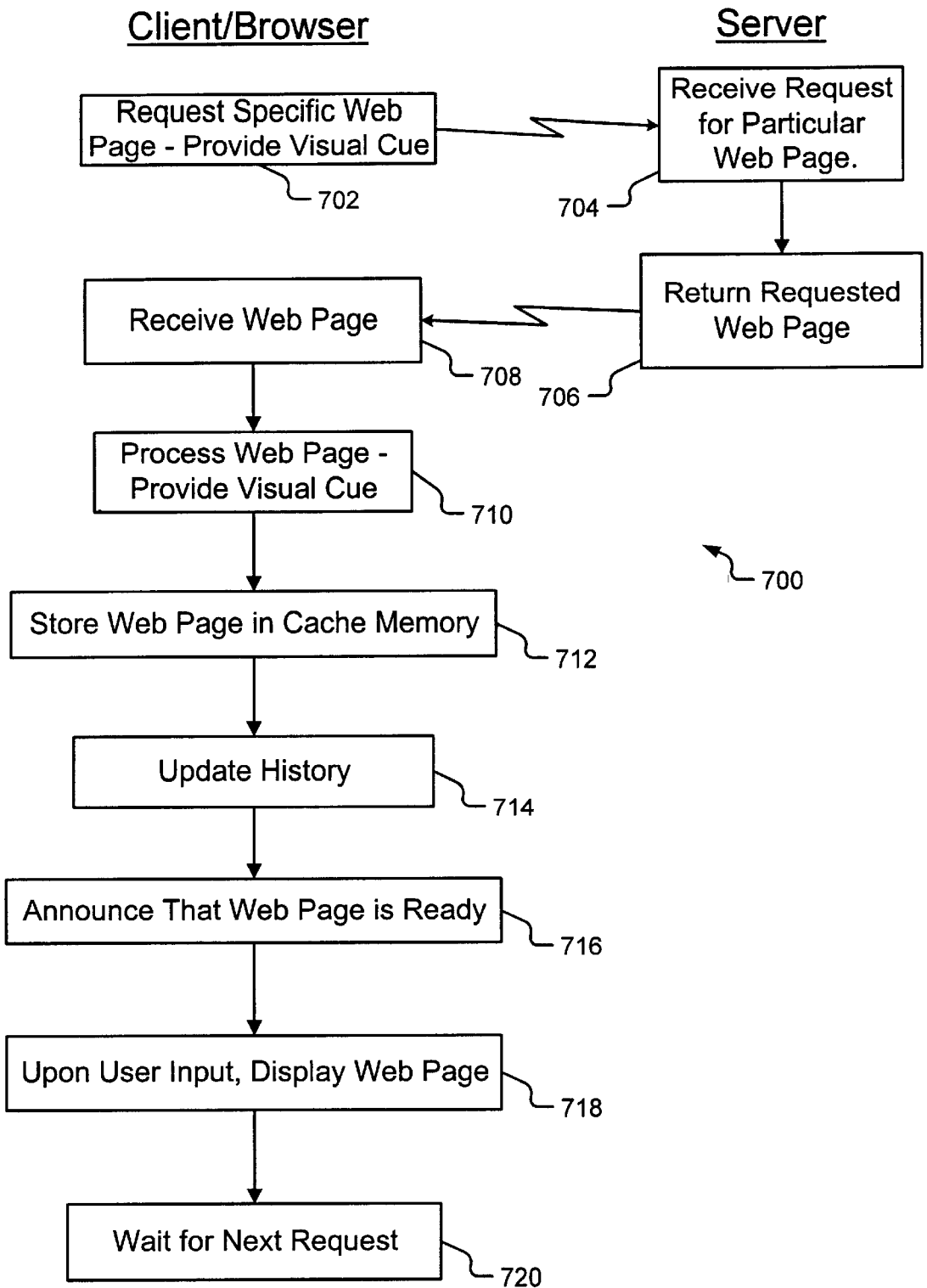
FIG. 7 is a flow diagram showing the operational characteristics of the present invention.

FIG. 7 illustrates the operational flow of one embodiment of the present invention. The process 700 begins with request operation 702 wherein the browser requests a URL from the server. The request may be initiated by the user or triggered by some other action occurring in the computer. The browser makes the request using network software 306 through communication connection using a predetermined protocol, as is known to one skilled in the art. Operation 702 may also send a command to the display module 312 to display an icon or other representation that a request for a web page is being processed, such as the new address bar 416 (FIG. 4).

Receive operation 704 occurs at the server and receives the request from the browser. Once the request is received, conduct operation 706 conducts the desired web page back to the requesting browser. Receive operation 708 occurs at the browser computer system and receives the web page conducted by the server over the network. A visual indication can be displayed to indicate the web page has been received. Additionally, a visual indication can display whether an error occurred in receiving the page, such as by changing the color of an associated hyperlink to a predetermined color. In essence, if an error occurred, such as a "file not found" error, the user might not know about the error unless an error-type indicator is displayed to the user. For these types of errors, the process flow may simply skip to operation 720, wherein the browser waits for the next request.

Once received, the browser then processes the web page at process operation 710. Processing the web page relates to the compiling of the HTML code into a form of object code that can be rendered to the display of the computer system. During the processing phase 710, the user may view a processing icon or some other visual indication to the user that the requested web page is being processed. Moreover, the processing icon may incorporate movement or color shift or some other variable visual indication that illustrates the processing action.

Following process operation 710, store operation 712 stores the object code generated at operation 710 into cache memory 320 shown in FIG. 3. Next, update history step 714 adds a reference to the history list, wherein the reference is associated with the portion of code stored in cache memory related to the web page. Update history step 714 provides the necessary link between the user-interface and the processed/stored code located in memory. In essence the user must be provided access to the code to eventually render the code to the display.

Once the update history step 714 is complete, announce step 716 announces to the user the fact that the web page has been processed (operation 710) and is accessible (step 714). Until the processed page is accessible, the user may view the processing icon. The announce step 716 may be performed in many different ways. For example the forward button may change colors, an icon may stop moving or otherwise indicate the web page is ready for viewing. Alternatively, if the URL was requested using a link from within an existing web page, the web page can change color from a "processing color" to a different color indicating that the web page is ready for viewing. Also, the entire page can flash to indicate the processing is complete. Moreover, a sound or other indicator can be employed. Essentially, any means of indicating the completion of the processing step may be used to communicate such information the user. Alternatively, the new page could be drawn automatically that instant.

Following the announce step 716, the browser waits for the user to initiate the display of the requested web page at display operation 718. Upon user input of a request to view the next web page, the browser displays the web page in the one window display using the reference in the history list and the code stored in cache. The requested web page replaces the previously displayed web page in a known manner. Since the code has already been processed, the next web page can be displayed relatively quickly. The user has significant control as to when a page is displayed since operation 718 waits for user input.

In an alternative embodiment, the user may request another web page while the process 700 is being executed. In such a case, the process step 702 requests the next web page as soon as it can following the receipt of the last requested web page at 708. Furthermore, the second web page can be requested in "parallel" to the first requested web page. There is no need to serialize this, as the browser is capable of opening as many streams as necessary to pull data from the server. When operating in parallel, the web pages may return in reverse order of their request, depending on which site is faster. While process steps 702, 704, 706 and 708 are operating, the remaining operations 710, 712, 714, 716 and 718 continue to process so the user may display the first requested web page as soon as possible.

In accordance with another aspect of this invention, the user may configure the browser to turn off the feature of background fetch. In yet another embodiment of the invention, the history list is updated after the web page has been substantially processed, as opposed to fully processed. Substantially processed web pages have been processed to the point that some of the information (e.g., text information) is ready to be displayed, for users who are more interested in viewing some portion of the next page than the current page. Moreover, the user may configure the browser to provide the visual cue following different degrees of processing. In yet another embodiment, the visual cue itself provides information related to the amount of processing that is complete so the user can determine when to switch to the next page.

The user may control the default fetching behavior of the browser. For example, the browser may be configured to automatically fetch subsequent web pages either in the background or directly. Additionally, the browser can be configured so that a single tap on a link fetches the associated web page directly, but double tapping the link causes the web page to be fetched in the background. Alternatively, a context menu or other mechanism may be used to access background fetch as a secondary way of fetching pages. In yet another embodiment, the browser may have an internal timer which is used to distinguish quickly loading web pages from the slower loading pages. Upon distinguishing the web pages, the browser can be configured to display quickly loading pages immediately and slower loading pages using background fetch.

The above described invention improves the browsing experience for users fetching and processing web pages in the background. This process decreases the amount of time that the users views white space or a blank screen. Moreover, it provides the user control as to when the next web page is displayed. Although the present invention greatly improves browsing on single window interfaces, such as small devices using Windows CE, the features described herein may be employed in multiple window operating systems as well. Users of multiple window systems do not have to switch between active windows, instead they merely need to select the Forward control to view the next web page.

Although the invention has been described in language specific to structural features and/or methodological steps, it is to be understood that the invention defined in the appended claims is not necessarily limited to the specific features or steps described. For example, although the description relates generally to browsing web pages, the process of opening other documents within the same window may consume processing time, such as opening a second word processing document (e.g., the time it takes to load the file into RAM from a disk drive may be considerable.) The principles outlined herein may apply to these other environments, wherein the second document is loaded in the background and, when loaded, an announcement is made to the user indicating its status. Thereafter a selection of an icon displays the next document in the desired window. Due to these other possible environments, it should be understood that the specific features and steps disclosed herein relate to preferred forms of implementing the claimed invention.

What is claimed is:

1. In a computer system having a display and memory, a method of displaying a subsequent page in place of a current page in a window of a graphical user interface on the computer display, said method comprising:
    receiving a user initiated process request for the subsequent page;
    processing the subsequent page into displayable form in memory;
    displaying a visual cue to a user indicating that the subsequent page has been substantially processed;
    receiving an indication from the user indicating that the subsequent page should be displayed; and
    displaying the subsequent page in the current window from memory.

2. A method as defined in claim 1 wherein the page is a web page and the computer is a client computer system that is connected to a server computer and wherein the server computer is adapted to receive a request for the web page from the client computer and return the web page to the client computer.

3. A method as defined in claim 2, wherein the client computer:

receives multiple requests for web pages to be fetched in the background;

upon receipt of a request for a web page, adds the requested web page to a history list;

provides the user access to the history list, allowing the user to select a web page for display from the web page; and if an error is returned to the client computer in place of a requested web page, the client computer removes the web page from the history list and provides a visual indication to the user that the requested web page is inaccessible.

4. A method as defined in claim 1 further comprising:
    following the processing step, adding a reference associated with the displayable web page in memory to a history list; and
    wherein the indication received from the user relates to the reference in the history list.

5. A method as defined in claim 4 wherein the reference is inserted in the middle of the history list.

6. A method as defined in claim 1 wherein the visual cue is displayed once the page has been fully processed.

7. A method as defined in claim 1 wherein the degree of processing required prior to displaying the visual cue may be configured by the user.

8. A method as defined in claim 1 wherein the visual cue provides information related to the amount of processing that has been completed.

9. A method as defined in claim 1 wherein the user interface displays a forward control and the visual cue is a visual change in the forward control.

10. A graphical user interface for a computer system, the graphical user interface having a display module for displaying a requested page in a current window, said graphical user interface comprising:
    a page request control that allows a user to request a particular page;
    a background fetch module that requests the page from a source and receives a response from the source, the background fetch module requesting the page in response to a user initiated request;
    a processing module that processes the response from the source;
    an announcement display module which announces the receipt of the page; and
    a display control selectable by a user that conducts a display signal to the display module to display the processed page, wherein a currently displayed page remains visible until a display signal is conducted by the display control.

11. A system for fetching a web page in the background comprising:
    a user interface displaying a current window and receiving a user initiated request for a web page;
    a requesting module requesting one or more web pages from one or more sources, wherein the act of requesting one of the web pages is in response to the user initiated request for the web page;
    a receiving module receiving the requested web page;
    a processing module processing the received web page;
    an announcement module announcing the completion of the processing of the received web page to the user;
    a display control for receiving an indication from the user that the subsequent web page should be displayed; and a graphical user interface for receiving a control signal from the display control, the display control signal causing the display of the processed web page in the current window.

12. A system as defined in claim 11 wherein the processing of the received web page does not interrupt the current display.

13. A computer program product readable by a computer and encoding instructions for executing a computer process for retrieving web pages and displaying the web pages in a current window on a computer display, the process comprising:

receiving a user initiated process request for a web page;

processing the web page into displayable form in memory;

displaying a visual cue to a user indicating that the subsequent page has been substantially processed;

receiving an indication that the subsequent page should be displayed; and displaying the web page in the current window from memory.

14. A computer program product as defined in claim 13 further comprising:

adding a reference associated with the web page in memory to a history list; and wherein the indication received from the user relates to the reference in the history list.

15. A computer program product as defined in claim 13 wherein the visual cue is displayed once the page has been fully processed.

16. A computer program product as defined in claim 13 wherein the visual cue provides information related to the amount of processing that has been completed.

17. A computer program product as defined in claim 13 wherein the user supplies the indication by selecting a forward button.

18. A computer program product as defined in claim 13 wherein the process further comprises:

upon displaying the visual cue to the user, waiting for user interaction for a predetermined interval;

if there is no user interaction within the interval, displaying the web page; and if there is user interaction within the interval, displaying the web page following an indication from the user that the subsequent page should be displayed.

* * * * *